US012137941B2

United States Patent
Venturini et al.

(10) Patent No.: US 12,137,941 B2
(45) Date of Patent: Nov. 12, 2024

(54) ORTHOPEDIC CABLE BONE TRANSPORT DEVICE AND BONE TRANSPORT SYSTEM COMPRISING SAID DEVICE

(71) Applicants: Orthofix S.R.L., Verona (IT); Texas Scottish Rite Hospital for Children, Dallas, TX (US)

(72) Inventors: Daniele Venturini, Povegliano Veronese (IT); Andrea Ottoboni, Giacciano con Baruchella (IT); Michael Lupatini, San Martino della Battaglia (IT); John D. Ross, Ovilla, TX (US); Mikhail L. Samchukov, Coppell, TX (US); Alexander M. Cherkashin, Flower Mound, TX (US); Karen D. Standefer, Flower Mound, TX (US)

(73) Assignees: Orthofix S.R.L., Verona (IT); Texas Scottish Rite Hospital for Children, Dallas, TX (US)

( * ) Notice: Subject to any disclaimer, the term of this patent is extended or adjusted under 35 U.S.C. 154(b) by 0 days.

(21) Appl. No.: 17/560,789

(22) Filed: Dec. 23, 2021

(65) Prior Publication Data
US 2023/0200854 A1   Jun. 29, 2023

(51) Int. Cl.
*A61B 17/64* (2006.01)
*A61B 17/66* (2006.01)
(Continued)

(52) U.S. Cl.
CPC .......... *A61B 17/6441* (2013.01); *A61B 17/66* (2013.01); *A61B 17/7216* (2013.01); *A61B 2017/00137* (2013.01)

(58) Field of Classification Search
CPC ..... A61B 17/8869; A61B 17/62; A61B 17/64; A61B 17/7053; A61B 17/8861;
(Continued)

(56) References Cited

U.S. PATENT DOCUMENTS

| 4,570,618 A | 2/1986 | Wu |
| 4,622,960 A | 11/1986 | Tam |

(Continued)

FOREIGN PATENT DOCUMENTS

| CN | 111789668 A | * 10/2020 |
| EP | 2772215 A1 | 3/2014 |

(Continued)

OTHER PUBLICATIONS

Rosteius Thomas et al. "Ilizaroy bone transport using an intramedullary cable transportation system in the treatment of tibial bone defects" Article, Jun. 1, 2021, 1606-1613, vol. 52(1), Elsevier, Amsterdam, Netherlands, 7 pages.

(Continued)

*Primary Examiner* — Julianna N Harvey
*Assistant Examiner* — Anna V. Little
(74) *Attorney, Agent, or Firm* — Haynes and Boone, LLP

(57) ABSTRACT

An orthopedic bone transport system includes an external fixation frame and a cable pulling device. The external fixation frame is attachable to a fixed bone segment with the external fixation frame oriented in a first plane. The cable pulling device includes a main body configured to be secured to the external fixation frame, a reel, and a transmission. The reel is rotatable about said main body and configured to wind up a cable to be secured to a transport bone segment to move said transport bone segment towards said fixed bone segment. The main body is secured to the external fixation frame with an axis of rotation of the reel oriented substantially parallel to the first plane, the axis of rotation of the reel thereby substantially lying on a transverse plane with respect to the fixed bone segment. The transmission drives the reel in order to wind up the cable.

20 Claims, 12 Drawing Sheets

(51) Int. Cl.
*A61B 17/72* (2006.01)
*A61B 17/00* (2006.01)

(58) Field of Classification Search
CPC . A61B 17/66; A61B 17/7216; A61B 17/6441; A61B 17/645; A61B 17/6458; A61B 17/6466; G10D 3/14
USPC .......................................................... 84/306
See application file for complete search history.

(56) References Cited

U.S. PATENT DOCUMENTS

| | | | | |
|---|---|---|---|---|
| 5,626,579 | A * | 5/1997 | Muschler | A61B 17/7216 606/62 |
| 5,863,292 | A * | 1/1999 | Tosic | A61B 17/6441 606/56 |
| 6,030,162 | A | 2/2000 | Huebner | |
| 6,033,412 | A | 3/2000 | Losken et al. | |
| 6,491,714 | B1 | 12/2002 | Bennett | |
| 8,162,979 | B2 * | 4/2012 | Sachs | A61B 17/7041 606/264 |
| 2004/0210227 | A1 | 10/2004 | Trail et al. | |
| 2005/0043734 | A1 * | 2/2005 | Kay | A61B 17/8863 606/301 |
| 2006/0235384 | A1 * | 10/2006 | Rovesti | A61B 17/62 606/56 |
| 2011/0313418 | A1 * | 12/2011 | Nikonovas | A61B 17/66 606/56 |
| 2013/0190830 | A1 | 7/2013 | Champagne et al. | |
| 2014/0350602 | A1 * | 11/2014 | Seme | A61B 17/7053 606/264 |
| 2017/0215922 | A1 * | 8/2017 | De Oto | A61B 17/645 |
| 2017/0238967 | A1 * | 8/2017 | Bordeaux | A61B 17/62 |
| 2018/0325557 | A1 * | 11/2018 | Suddaby | A61B 17/8076 |
| 2019/0110814 | A1 * | 4/2019 | Nemovicher | A61B 90/57 |
| 2019/0133654 | A1 | 5/2019 | Murali | |
| 2021/0228239 | A1 * | 7/2021 | Sanders | A61B 17/6466 |
| 2021/0322060 | A1 * | 10/2021 | Barrett | A61B 17/701 |

FOREIGN PATENT DOCUMENTS

| | | | |
|---|---|---|---|
| EP | 3560446 | A1 | 10/2019 |
| GB | 2207055 | A | 1/1989 |
| WO | WO-9948414 | A2 * | 9/1999 ............ A61B 17/62 |
| WO | 2009109371 | A2 | 9/2009 |
| WO | 2011097672 | A1 | 8/2011 |
| WO | 2016174420 | A1 | 11/2016 |
| WO | 2019168817 | A1 | 9/2019 |
| WO | 2022240692 | A1 | 11/2022 |

OTHER PUBLICATIONS

European Patent Office "European Search Report," for Application No. EP 21217240, May 9, 2022, 2 pages.

International Search Report and Written Opinion for Application No. PCT/EP2022/087716, mailed May 26, 2023, 29 pages.

* cited by examiner

ORTHOPEDIC CABLE BONE TRANSPORT DEVICE AND BONE TRANSPORT SYSTEM COMPRISING SAID DEVICE

TECHNICAL FIELD

The present invention is generally directed to a cable pulling device and an associated orthopedic bone transport system.

The invention therefore has a useful application in the sector of orthopedics, in particular in bone defects treatment.

BACKGROUND OF THE DISCLOSURE

External fixation systems are used in a variety of surgical procedures including fracture reduction, limb lengthening, and deformity correction, as well as treatment of non-unions, mal-unions, and bone defects. For bone defects treatment, a rigid framework comprising of upper (proximal) and lower (distal) external circular supports is placed externally around an affected limb and attached to associated upper (proximal) and lower (distal) bone segments using wires and/or pins. The proximal and distal external supports of the rigid framework are interconnected by threaded or telescopic rods stabilizing aligned spatial positioning of the distal bone segment relative to the proximal bone segment. One of those bone segments (e.g., proximal) is then divided into two bone segments (e.g., via osteotomy), thereby producing a third (intercalary) bone segment also called a transport bone segment that is gradually transported through the bone defect area creating newly formed bone tissues in the path of that transportation.

It is beneficial to have a stable fixation of the transport bone segment for controlled movement of that transport bone segment through the area of bone defect with minimal penetration of surrounded soft tissues by fixation wires and/or pins. For example, it may be beneficial to secure the transport segment to a separate intercalary external support (e.g., transport external support) via transverse wires and/or pins and gradually move that intercalary support with attached transport bone segment along the rods interconnecting the proximal and distal external supports (FIG. 1, transverse-wires bone transport). Although such structure provides sufficient stability of the transport bone segment fixation, it typically produces multiple long longitudinal cuts through the surrounding soft tissues by wires and/or pins potentially resulting in pain, infection, and other complications.

Stabilization of transport bone segment via two wires with stoppers obliquely inserted into transport bone segment have been sporadically used for bone transport. This method of bone defect treatment is known as the Ilizarov bone transport (FIG. 2, oblique-wires bone transport). Utilization of this method is significantly reduced recently due to several limitations including difficulties in insertion and removal of obliquely oriented wires into/from the transport bone segment, limited distance of transport bone segment transportation through the bone defect area, pressure of obliquely oriented wires on the surrounding soft tissues at the exit points, and potential longitudinal misalignment of the transport bone segment with the residual proximal and distal segments at the end of bone transport.

Stabilization of transport bone segment via cable have also been traditionally used for bone transport. This method of bone defect treatment is known as the Weber bone transport (FIG. 3, Weber cable bone transport with rollers and gradual cable pulling rods). In those cases, a thin 1.8 mm diameter stainless-steel cable is inserted through the end of the transport bone segment, placed longitudinally parallel to the path of the transport bone segment movement, exiting out at the level of docking between the transport bone segment and one of the residual bone segments (e.g., distal bone segment). The ends of the cable are then placed into grooves of the special plastic rollers redirecting the ends of the cable towards proximal external support and attached to threaded or telescopic rods providing gradual pull of the cable with attached transport bone segment through the area of bone defect. An enhanced version of the Weber cable bone transport, known as the Balanced Cable Bone transport, was recently introduced by Dr. Stephen Quinnan.

Although cable bone transport significantly reduced soft tissue related complication, the process of transport bone segment transportation using path redirection rollers and threaded rods for gradual adjustment located far away from the rollers is very complicated. In addition, rollers and pulling rods occupy space on the external supports limiting places for other connecting and wire/pin fixation elements. Finally, the cable ends located between the proximal and distal external supports are unprotected and can be damaged from the outside failing to provide sufficient stability of transport bone segment fixation.

The technical problem underlying the present invention is therefore that of devising a cable bone transport systems that solves at least some of the drawbacks of the prior art, and in particular which provides sufficient stability of the transport bone segment, minimizes number of external components between the proximal and distal external supports, and simplifies transportation of the intercalary transport bone segment during the bone transport.

SUMMARY OF THE INVENTION

The idea for a solution forming basis of the present invention is that of proposing a device, which uses a mechanical transmission driving by small increments a reel that pulls the cable to which the transport bone segment is attached.

By means of such a device, a new bone transport technique can be implemented, wherein the cable enters at a first the intercalary transport bone segment at its resected end and is attached thereto by means of an external loop, passing through at least one tangential hole made on the transport bone segment into its intermedullary canal and bone defect area following the bone axis and the pass of the movement of the transport bone segment, enters the residual bone segment (proximal or distal) from the intermedullary canal and, after orthogonal redirection around a fulcrum pin or screw, exits that residual bone segment, surrounding soft tissues and skin to be attached to the cable pulling device.

The aforementioned technical problem is therefore solved by a cable pulling device for an orthopedic bone transport system, comprising: a main body configured to be secured to an external fixation frame solidly attached to at least one fixed bone segment; a reel rotatable about said main body, for winding up a cable to be secured to a transport bone segment, thus moving said transport bone segment towards said fixed bone segment; a transmission mechanism driving the reel in order to wind up the cable.

The reel and the related transmission mechanism therefore define a winch acting on the cable connected to the transport bone segment: by driving the winch, the cable is pulled, and the transport bone segment is approached to the fixed bone segment.

Preferably, the reel is only rotatable in a single direction, so that the tension on the cable cannot be released by winding it out.

In a preferred embodiment, the main body is a case which houses at least partially the transmission and the reel.

Preferably, the transmission mechanism is a worm gear mechanism. The worm gear mechanism may define an irreversible kinematic pair, meaning that the motion can be transmitted from an input worm to an output worm gear but not from the worm gear to the worm.

Preferably, the worm gear mechanism comprises: a worm rotatably fixed to the main body; and a worm gear rotatably fixed to the main body and engaging with said worm, wherein said reel integrally rotates with said worm gear.

Preferably, wherein the worm gear is coaxially provided with the reel.

The cable pulling device may further comprise a knob to transmit a rotating motion to said worm. In particular, the knob can be periodically rotated by a user—preferably a healthcare practitioner—to displace the transport bone segment toward the fixed bone segment by a predefined increment.

Preferably, the knob is mounted on the same shaft of the worm. The knob can be free to axially slide on said shaft between an extracted position and a retracted position.

Preferably, the knob has a locking mechanism that locks the rotation of the knob with respect to the main body at given locking angular positions of the knob. These locking angular positions may correspond to fixed angular increments that translate into predefined incremental displacements of the transport bone segment. In this manner, the locking mechanism guides the user into applying the right amount of displacement to the transport bone segment.

The fixed angular increments may correspond to one fourth of a turn (i.e. 90°), one sixth of a turn (i.e. 60°), one eighth of a turn (i.e. 45°), or may correspond to yet another increment.

Preferably, the predefined linear increment in the cable displacement is comprised between 0.25 and 0.5 mm In the specific case of a knob angular increment of one sixth of a turn, this is given by the formula d=(D·π)/6·n, wherein D is the diameter of the reel and n is the transmission ratio of the transmission mechanism. Obviously, the formula should be modified for the alternative angular increments given above.

Preferably, the diameter D of the reel is between 25 mm and 50 mm, most preferably it is equal to about 30 mm (28.6 mm), resulting in 90 mm of circumference of the reel.

In a preferred embodiment, the locking mechanism comprises a regular polygon boss and a mating recess, respectively provided on the knob and on the main body, or the other way around. The rotation of the worm is prevented when the regular polygon boss is pressed into the recess, which happens because of the action of an elastic element biasing the knob towards the main body. Therefore, to rotate the knob one has to extract it from the position in which the boss seats in the recess, and then the knob freely rotates until the next alignment position between boss and recess is reached.

A hexagonal boss and recess can be used to achieve a fixed angular increment of one sixth of a turn; correspondingly, squared or octahedral bosses and recesses could be employed for fixed angular increments of one fourth or one eighth of a turn; other polygonal shapes may be used for other angular increments.

As an alternative to manual activation, the cable pulling device might be activated by means of a motor. In particular, the motor can be automatically activated, for instance at preset time intervals.

The device can therefore comprise a motor coupled with the worm to drive the rotation of the worm and a controller for controlling the motor, wherein the controller is configured to control an activation frequency of the motor and a rotation angle of the worm driven by the motor for each activation of the motor.

Preferably, the cable pulling device comprises a pawl acting as a ratchet device, i.e. configured to prevent a reverse rotation of the worm gear under a force acting on the cable.

Preferably, the reel is provided with a radial hole through which the cable passes, and the cable is clamped by an end of a threaded shaft integral with the worm gear.

Preferably, the reel comprises a spiral groove on its external surfaces to receive the cable as it winds up, preventing overlapping.

In a possible embodiment, the cable pulling device comprises a force sensor for sensing a tension force acting on the cable. The force sensor may be directly or indirectly coupled to the cable. In other words, it may be placed on the cable itself or on other elements interacting with the cable, for instance on the reel.

The technical problem is also solved by a bone transport system, comprising: an external fixation frame configured to be attached to at least one fixed bone segment; and at least one cable pulling device as previously described, solidly attached to the external fixation frame; and means for redirecting the cable configured to be attached to the fixed bone segment and to redirect the cable departing from the cable pulling devices towards a bone transport segment.

Preferably, the bone transport system comprises two cable pulling devices solidly attached to the external fixation frame in diametrically opposite positions, wherein the two cable pulling devices hold the opposite ends of a same cable.

Preferably, the cable is configured to depart from the cable pulling devices, enter the fixed bone segment via lateral holes, redirect in an axial direction of the bone at the means for redirecting the cable, enter the bone transport segment, exit the same bone transport segment via at least one lateral hole, loop around said bone transport segment.

Features and advantages of the present invention will be disclosed with reference to the enclosed drawings relating to an indicative and a non-limiting implementation example.

DETAILED DESCRIPTION

Figure 1:
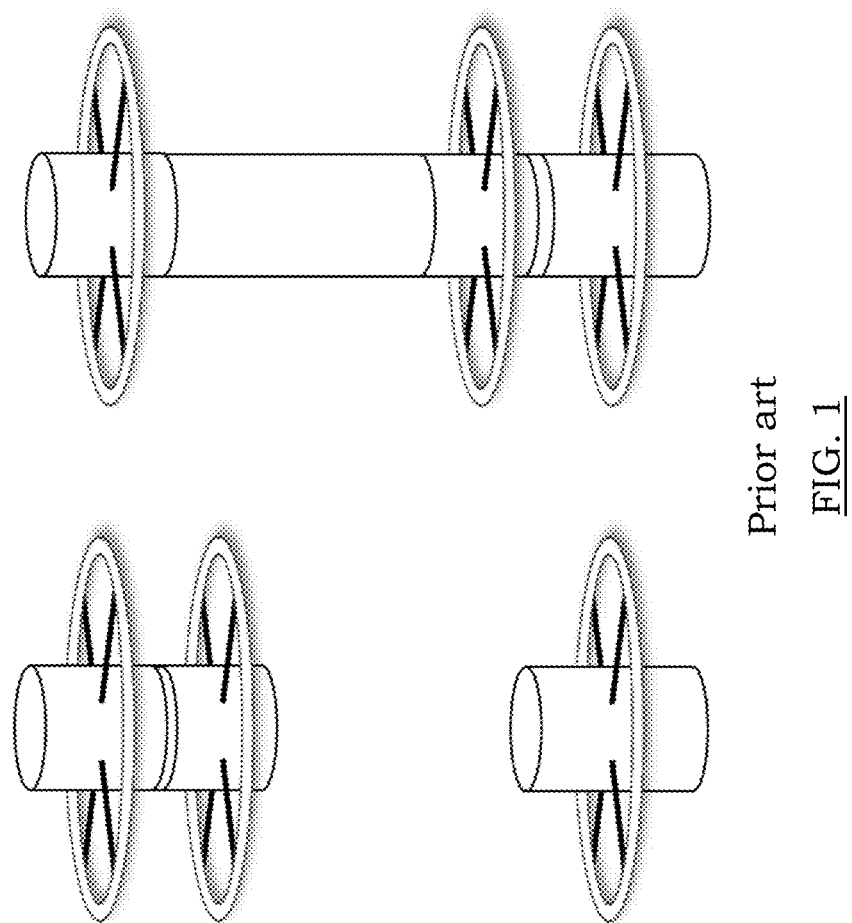
FIG. 1 shows an example of a transverse-wires bone transport technique according to the prior art.
Figure 2:
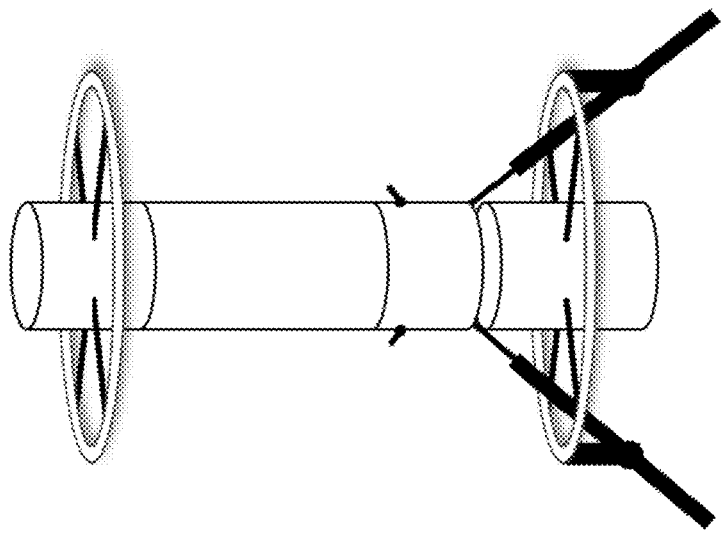
FIG. 2 shows an example of an oblique-wires bone transport technique according to the prior art.
Figure 2:
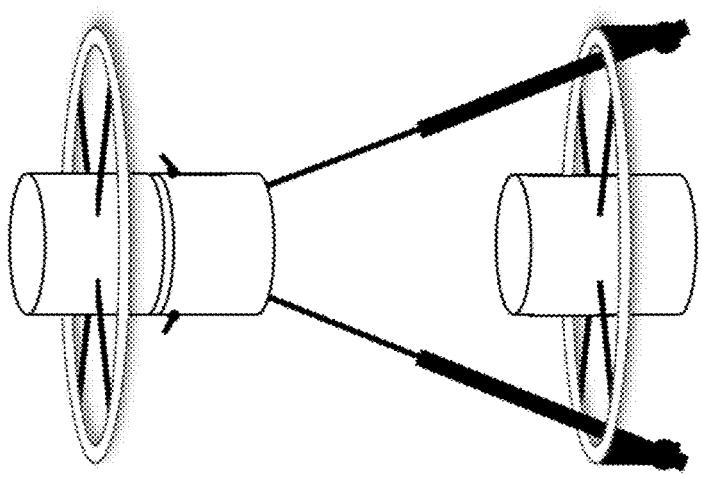
Figure 3:
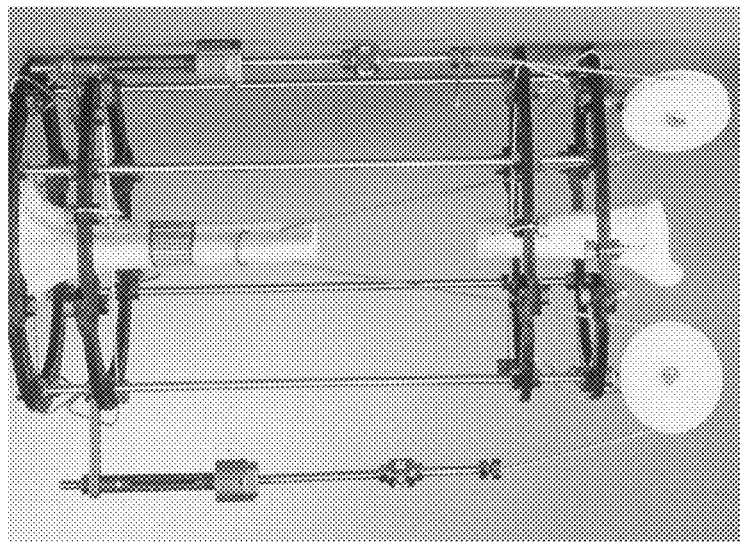
FIG. 3 shows an example of a Weber cable bone transport technique, with rollers and gradual cable pulling rods according to the prior art.

In the following detailed description, reference is made to the accompanying drawings that form a part hereof and in which is shown, by way of illustration, specific embodiments. In the drawings, like numerals describe substantially similar components throughout the several views. Other embodiments may be disclosed, and structural changes may be made without departing from the scope of the present disclosure. The following detailed description is, therefore, not to be taken in a limiting sense.

The present disclosure relates to a segmental bone transport system 1 which adopts an innovative technique based on the pulling of a cable 9 by a reel 8.

The bone transport system 1 is designed to apply a translation force to a transport bone segment 10 by decreasing the length of a flexible cable 9 that is attached to that transport bone segment 10. To do so, it adopts a concept which is similar to that used to tune stringed instruments. One end of the cable 9 is secured to a reel 8 onto which it is wound via a worm gear mechanism 4.

In the case of a musical string, the other end of the string is fixed and not allowed to translate. As the tuning mechanism is turned, the tension of the string is changed which also changes it resonate frequency. The worm gear mechanism ensures that the tension will be maintained when the mechanism is no longer being turned. The worm can turn the worm gear to tighten the cable, but the worm gear cannot turn the worm to release the tension on the cable.

In the bone transport system 1 according to the current invention, tensioning the cable 9 by shortening it causes the bone transport segment 10 to move. The distance that the bone transport segment 10 can travel is a function of how much cable 9 can be wind around the reel 8.

Bone segment transport is performed in steps where the distance of transport for each step is preferably 0.25 to 0.50 mm performed two to four times a day. In most cases, a total of 1.0 mm of transport distance per day is desired.

The preferred embodiment of the invention herein described is configured to shorten the cable 0.25 mm for each one sixth turn of an activation knob 12.

To ensure that the knob 12 is not accidentally turned between adjustments, a spring-loaded locking mechanism, which will be better described in the following, secures the knob at each 60° turn increment.

Like the instrument tuning key, the worm gear mechanism 4 is used to ensure that the cable does not reverse direction under load. The reduction ratio of the worm gear mechanism 4 and the diameter of the reel 8 determine the amount of length change of the cable for a given activation increment of the knob 12.

An appropriate reel diameter can be derived with the following equation: Reel Diameter=(Increments per revolution) (increment distance per activation) (gear reduction)/$\pi$. The ideal reel diameter for this device was determined to be 28.648 mm This diameter was found to be large enough to allow the relatively stiff cable 9 to wind flat on it but not so large to be bulky and require more than a single set of reduction gears.

To ensure a uniform rate of transport, it is important to ensure that the cable 9 does not wind on top of itself. To ensure that this does not happen, the reel circumference contains a spiral groove 34 to guide the cable 9 and prevent it from overlapping.

The transport distance for each revolution of the reel is a function of the reel circumference. For this device which has a reel diameter of 28.648 mm, the circumference would be $\pi \cdot 28.648$ mm=90 mm Therefore, each full turn of the reel 8 would shorten the cable by 90 mm and move the bone transport segment 10 by the same amount of distance.

The cable 9 is secured to the reel by passing through an oblique radial hole 32 and then clamped in place by an end of an axial screw 26. Excess cable is cut off prior to starting the transport process.

The worm gear mechanism 4 with the reel 8 are comprised in a cable pulling device 1 and substantially contained in a main body 2 or case.

The main body 2 is attached by means of a bolt 14 to a distal ring 38 of an external fixation frame. The bolt 14, which has an interposed washer 45, allows the position distance of the device with respect to the skin to be adjusted when the device is attached to said ring 38.

Figure 9:
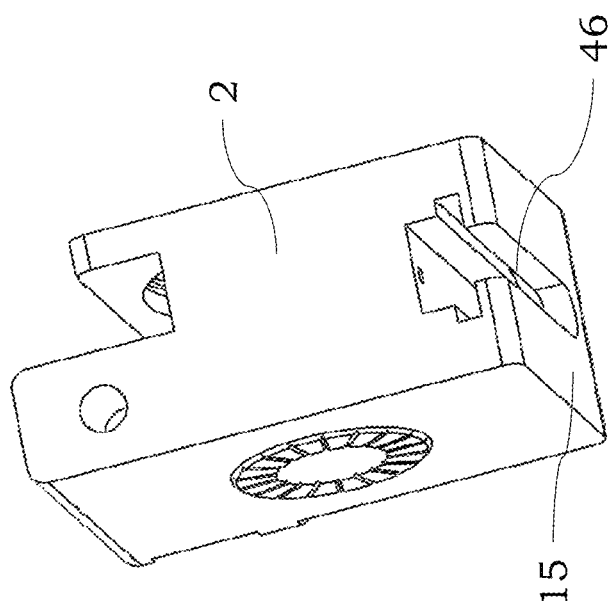
FIG. 9 shows a perspective view of a detail of a main body in the form of a case of the cable pulling device of FIG. 4.

As visible in FIG. 9, The main body 2 has an elongated slot 46, which extends in a transverse direction and receives the mounting screw 14 and the washer 45.

The cable pulling device 1 employed in the bone transport system is described below in further detail, with reference to enclosed FIGS. 4-11.

Figure 4:
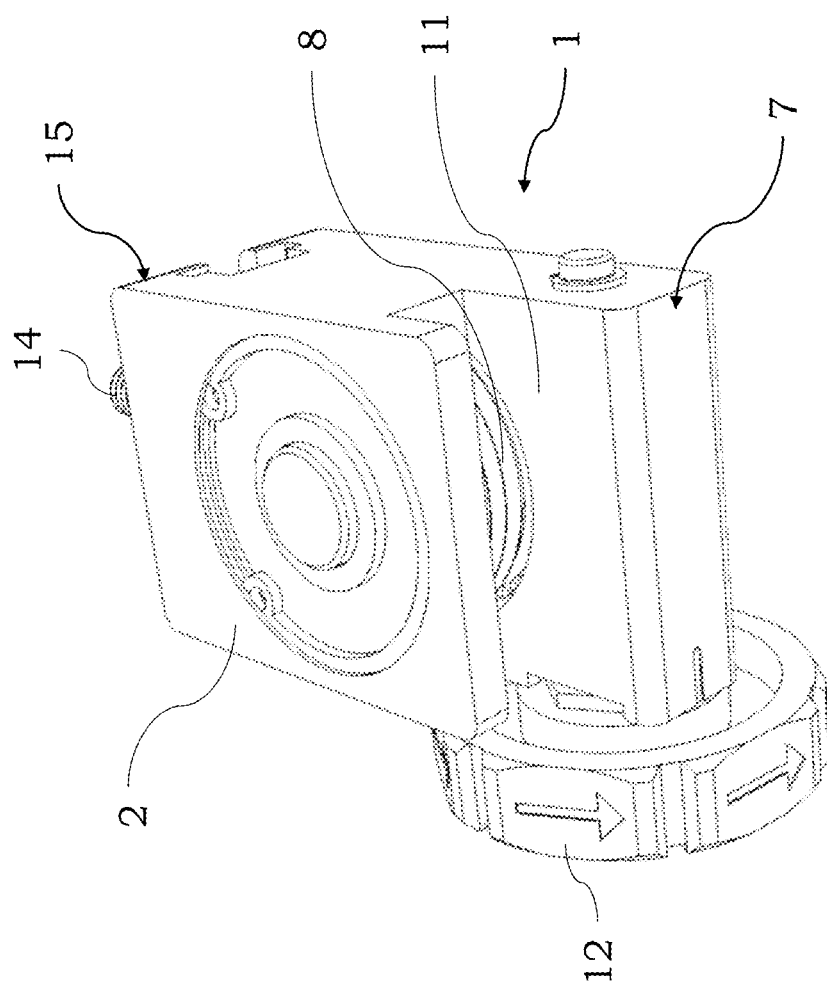
FIG. 4 shows a perspective view of a cable pulling device for bone transport according to an embodiment of the present invention.

As visible in FIG. 4, the cable pulling device 1 comprises the main body 2 and a worm gear mechanism 4 arranged in the main body 2.

Figure 5:
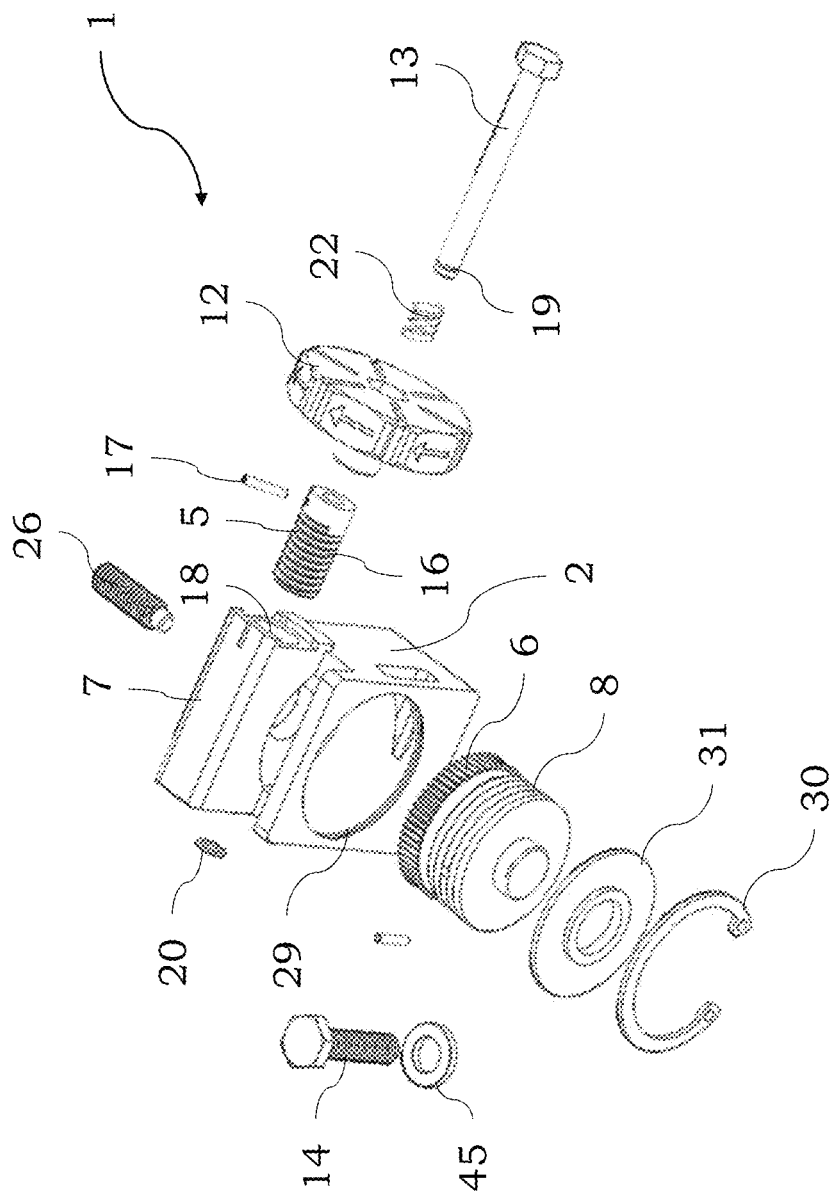
FIG. 5 shows an exploded view of the cable pulling device of FIG. 4.

As visible in FIG. 5, the worm gear mechanism 4 comprises a worm 5 and a worm gear 6. The worm 5 is rotatably fixed within an end portion 7 of the main body 2, wherein the worm gear 6 is rotatably fixed in a central portion of the main body 2 and engages with the worm 5.

The worm gear 6 is coaxially coupled with a reel 8. When the cable pulling device 1 is in use, one end of a cable 9 is secured to a transport bone segment 10, and the other end of the cable 9 is secured to the reel 8. The worm gear mechanism 4 rotates the reel 8 and winds up the cable 9, dragging the transport bone segment 10 toward a docking site.

As visible in FIG. 4, the main body 2 has at least an opening 11 to expose a lateral portion of the reel 8. The cable 9 passes through the opening 11 and winds on the reel 8. A knob 12 is provided for driving the worm 5 into rotation.

As visible in FIG. 5, the knob 12 is fitted on a same shaft 13 of the worm 5 and is therefore laterally placed on the same first end portion 7. The bolt 14 is at the second end portion 15.

The worm 5 comprises an externally threaded sleeve 16 which is locked on the shaft 13 by means of a set screw 17. The shaft 13 traverses a through-hole 18 with varying diameter of the main body 2. One end of the shaft 13, which emerges from outside the main body 2, is provided with an annular groove 19 for a locking O-ring 20.

Figure 11:
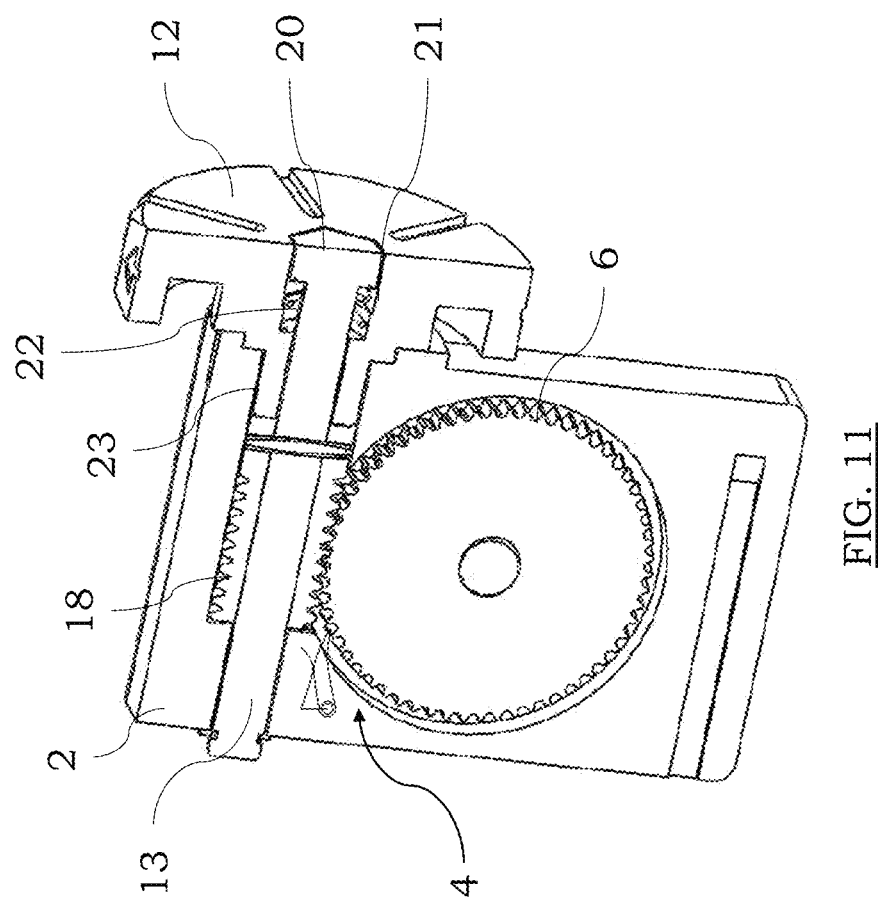
FIG. 11 is a cross-sectional view of the pulling device of FIG. 4 which emphasizes the ratchet mechanism acting on the worm screw.

As clearly visible in FIG. 11, the knob 12 is fixed at the other end of the shaft 13. The shaft 13 is in the form of a bolt, and a polygonal bolt head 20 of the shaft 13 mates with a corresponding seat 21 on the external face of the knob 12, such that the rotation of the knob 12 with respect to the shaft 13 is prevented. However, the knob 12 is free to move axially along the shaft 13. An elastic element 22 in the form of a spring is provided within the seat 21 between the knob 12 and the bolt head 20. Therefore, the knob 12 is pressed toward the main body 2 by the elastic element 22. The knob 12 is further provided with a nose portion 23 to be received in the through-hole 18 of the main body 2.

In the preferred embodiment herein described the outer outline of the knob 12 has a hexagon shape, and arrows are provided along an external rim of the knob 12 to indicate the direction along which the knob 12 is to be rotated. In this embodiment, the knob 12 is meant to be rotated by preset angular intervals of one sixth of a turn.

In the art of the present invention, bone segment transport is performed in steps where the distance of transport for each step is 0.25 to 0.50 mm performed two to four times a day. Mostly, a total of 1.0 mm of transport distance per day is desired. In this case, the cable pulling device 1 for bone transport may be configured to shorten the cable by 0.25 mm for each sixth turn of the knob 12. In the embodiment of the present invention, the worm 5 may be configured as a single-threaded worm, and the worm gear 6 may be provided with 60 teeth. Accordingly, the reduction ratio of the worm gear mechanism 4 is 60. The reduction ratio of the worm gear mechanism 4 and the diameter of the reel 8 can determine the amount of length change of the cable for a given activation increment of the knob according to the equation mentioned before. Therefore, the ideal diameter of the reel 8 can be determined to be 6*0.25*60/π, i.e., 28.648 mm Moreover, this diameter of the reel 8 has been found to be large enough to allow the relatively stiff cable 9 to wind flat on it but not so large as to be bulky and require more than a single set of reduction gears.

The specific dimension mentioned above is only for illustrative purpose, it should be appreciated that other dimensions can be adopted by those skilled in the art without departing from the scope of the present invention.

Figure 10:
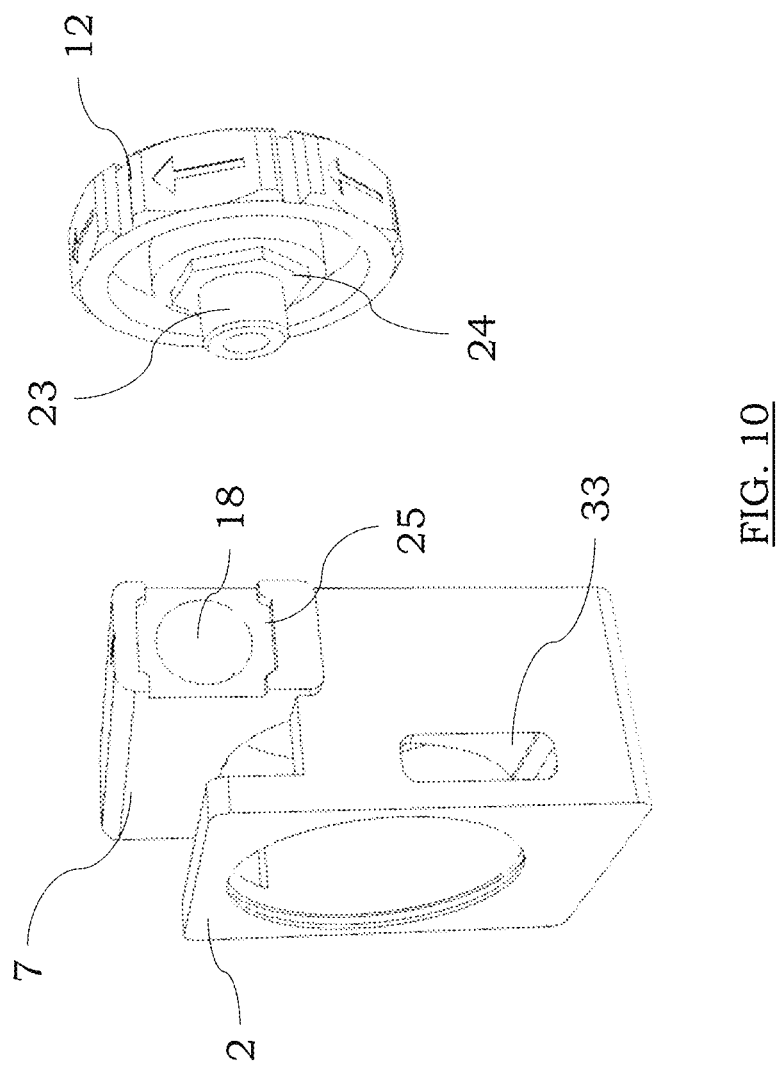
FIG. 10 shows an exploded view of a detail of the case and knob of the cable pulling device of FIG. 4.

As visible in FIG. 10, the knob 12 is provided with a regular polygon boss 24, and the main body 2 is provided with a recess 25 at a side of first end portion 7 thereof to receive the regular polygon boss 24 of the knob 12. The rotation of the worm 5 is prevented when the regular polygon boss 24 of the knob 12 is pressed into the recess 25 of the case 2. Since the elastic element 22 presses the knob 12 against the main body 2, the boss 24 of the knob 12 will be forced into the recess 25 of the case 2, forming a spring-loaded locking mechanism to prevent the rotation of the worm 5 and thus the worm gear 6 with the reel 8. Accordingly, it can be ensured that the knob 12 would be not accidentally turned between adjustments.

As seen above, the worm 5 can be rotated manually by rotating the knob 12. However, the present invention is not limited thereto. As an example, a motor (not shown) can be coupled to the shaft 13 of the worm 5 to drive the rotation of the worm 5. Further, a controller (not shown) can be also provided to control the motor. According to this non-illustrated embodiment, the controller can be configured to control an activation frequency of the motor and a rotation angle of the worm driven by the motor for each activation of the motor. Accordingly, the transport distance of the bone segment for each day can be controlled by the motor and the associated controller. In an embodiment of the present invention, the motor may be a stepper motor, and the controller may be a stepper motor driver, which are well-known by those skilled in the art.

Figure 8:
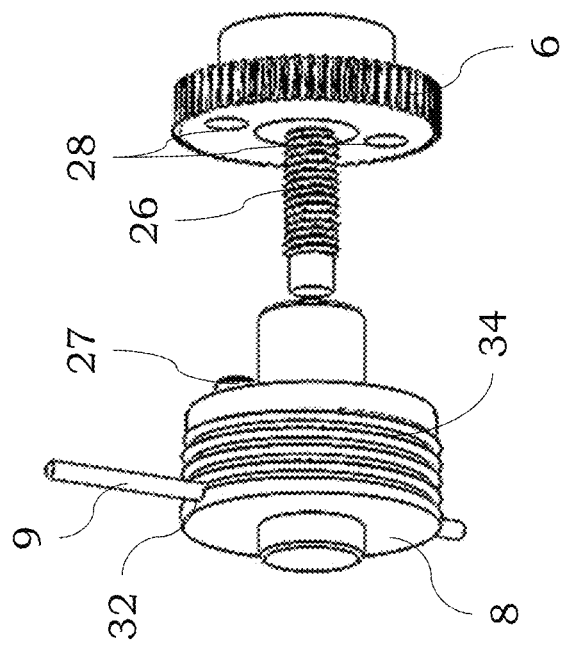
FIG. 8 shows an exploded view of a detail of a worm gear and reel in the worm gear mechanism of FIG. 7.

As visible for instance in FIG. 8, the worm gear 6 is coaxially coupled with the reel 8. The axial screw 26 is used to fix the cable 9 into the reel 8. The reel 8 can be provided with a number of eccentric alignment pins 27 which engage with a corresponding number of alignment holes 28 of the worm gear 6. In the preferred embodiment, two holes and pins are provided: however, a different number of holes and pins can be used, and the hole and pins can be reversed on the reel and gear.

Figure 6:
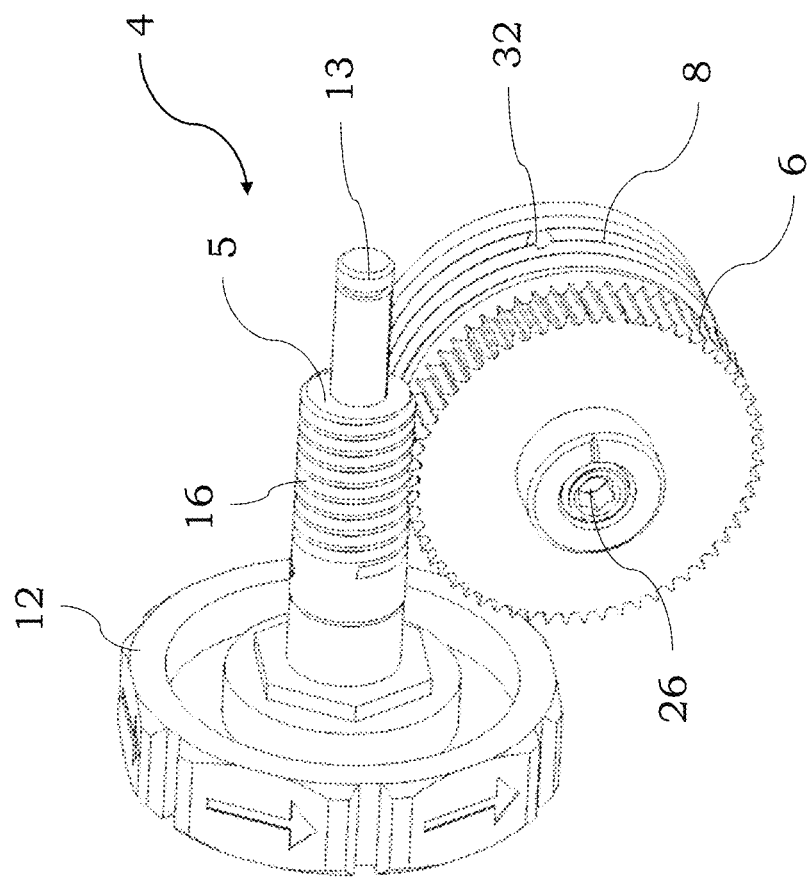
FIG. 6 shows a perspective view of a detail of a worm gear mechanism in the cable pulling device of FIG. 4.
Figure 7:
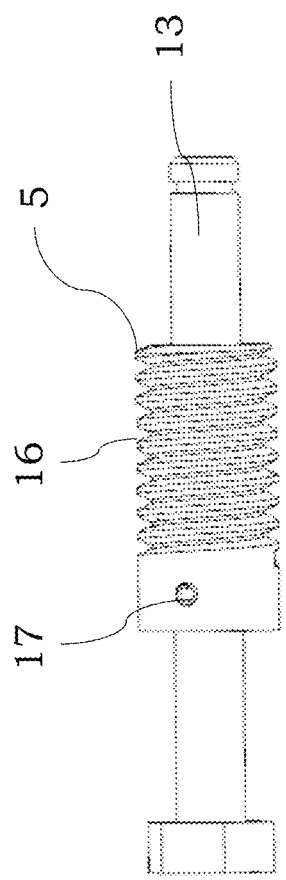
FIG. 7 shows a perspective view of a detail of a worm fitted on its corresponding shaft in the worm gear mechanism of FIG. 7.

As visible in FIG. 6, the worm gear 6 engages with the worm 5 to define the worm gear mechanism 4.

As visible in FIG. 5, a circular opening 29, with varying diameter, is provided in the main body 2 to house the worm gear 6 and the reel 8, the latter being locked into position by a snap ring 30 placed over a washer 31.

As previously mentioned and visible in FIG. 6, the reel 8 is provided with oblique radial hole 32 to facilitate the correct wire winding without overlapping. One end of the cable 9 is inserted into the radial hole 32, and then the cable 9 is clamped by the axial screw 26, thus securing it to the reel 8.

Any protruding part of the wire 9 can be cut at the opening 33 visible in FIG. 10. With the rotation of the reel 8, the cable 9 is wind around the reel 8.

To ensure a uniform rate of transport of the transport bone segment 10, it is important to ensure that the cable 9 does not wind on top of itself. To this end, the reel 8 contains a spiral groove 34 around its outer surface to guide the cable 9 and prevent the cable 9 from overlapping and the oblique radial hole 32. A transport distance for each revolution of the reel 8 is a function of the circumference of the reel 8. In an embodiment where the reel 8 has a diameter of 28.648 mm, the circumference would be π*28.648 mm or 90 mm In this case, each full turn of the reel 8 would shorten the cable 9 by 90 mm and move the transport bone segment 10 by the same amount.

In an embodiment of the present invention, which is not shown in the drawings, a force sensor may be attached to the cable 9 for sensing a tension force of the cable 9. The location of the fore sensor on the cable 9 can be determined according to the actual needs. According to the embodiment of the present invention, the force sensor can be used to sense the tension of the cable 9, which will allow to check if the formation of the callus takes place correctly. In addition, the amount of displacement can also be measured in order to support a biological function.

The worm gear 4 could have a ratchet mechanism which prevents reverse motion thereof. A ratchet mechanism of this kind, which is not strictly necessary in the preferred layout of the invention according to the enclosed Figures, could comprise a leaf spring acting on a locking pawl, which would be then biased towards the worm gear. Alternative forms of ratchet mechanisms could also be employed.

It should also be noted that any possible combination of the motor, the spring-loaded locking mechanism, and ratchet mechanism could be adopted in the present invention to prevent a reverse rotation of the worm gear 6 with the reel 8 under the load of the cable 9.

Figure 12:
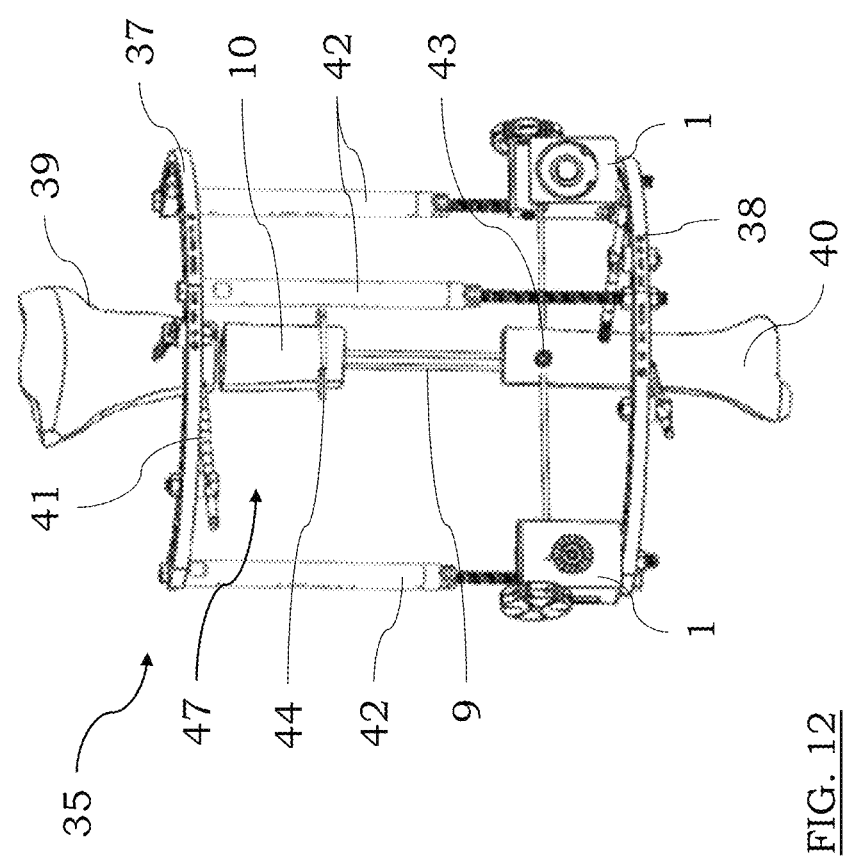
FIG. 12 shows a perspective view of a bone transport system according to the present invention.

FIG. 12 shows an example of a bone transport system 35 which is provided with cable pulling devices 1 for bone transport and attached to bone segments according to an embodiment of the present invention.

The bone transport system 35 according to the invention is meant to be applied to a long bone of a patient; in the depicted embodiment the long bone is a tibia.

The bone transport system 35 comprises an external frame 47 which features a proximal ring 37 and a distal ring 38. The proximal ring 37 and the distal ring 38 are respectively anchored to a proximal fixed bone segment 39 and to a distal fixed bone segment 40 by means of tensioned wires and/or fixation pins 41. The proximal ring 37 is connected to the distal ring 38 by means of longitudinal rods 42. Preferably, longitudinal rods 42 are extensible.

A transport bone segment 10 is axially comprised between the proximal fixed bone segment 39 and the distal fixed bone segment 40.

The bone transport system 35 comprises two cable pulling devices 1 which are attached via their bolts 14 at diametrically opposite sites on the distal ring 38. The cable pulling devices 1 are therefore placed laterally and medially with respect to the distal fixed bone segment 40. A cable 9 is pulled between the two cable pulling devices 1 and follows a path which will be described in the following.

The bone transport system 35 further comprises means 43 for redirecting the cable 9 at the distal fixed bone segment. Preferably, said means 43 for redirecting the cable 9 take the form of a fulcrum pin or screw which is implanted in the distal fixed bone segment 40, following an anterior-posterior direction.

The cable 9 enters the transport bone segment 10 at its resected end and is attached thereto by means of an external loop 44, passing through at least one tangential hole made on the transport bone segment 10 into its intermedullary canal and bone defect area following the bone axis, enters the fixed distal bone segment 40 from the intermedullary canal and, after orthogonal redirection around the fulcrum pin or screw 43, exits that distal bone segment 40 laterally.

As mentioned above, the cable 9 is symmetrically stabilized on the transport bone segment 10 by making the two ends exit axially into the medullary canal.

In the distal fixed bone segment 40, the two ends of the cable 9 rotate around the fulcrum pin 43 and exit the cortices one on one side and the other on the side placed in the position of the devices 1 in line with the reels 8.

The bone transport system 35 is implanted via a surgical method which can be derived from the structural description given above.

According to the present invention, the improved cable pulling device for bone transport can provide sufficient stability of the transport bone segment, minimize number of external components between the proximal and distal external supports. The bone transport system according to the invention callows guiding independently the movement on the two ends of the cable, which allows to orient the angulation of the transport bone segment during transport towards the fixed segment and simplifies transportation of the intercalary transport bone segment during the bone transport.

Although specific examples have been illustrated and described above, those of ordinary skill in the art will appreciate that an arrangement to achieve the same results can be substituted for the specific embodiments shown. This disclosure is intended to cover adaptations or variations of one or more embodiments of the present disclosure. It is to be understood that the above description has been made in an illustrative fashion, and not a restrictive one. The scope of one or more examples of the present disclosure should be determined with reference to the appended claims, along with the full range of equivalents to which such claims are entitled.

What is claimed is:

1. An orthopedic bone transport system, comprising:
    an external fixation frame attachable to a fixed bone segment with the external fixation frame oriented in a first plane; and
    a cable pulling device comprising:
        a main body configured to be secured to the external fixation frame;
        a reel rotatable about said main body and configured to wind up a cable to be secured to a transport bone segment to move said transport bone segment towards said fixed bone segment, wherein the main body is secured to the external fixation frame with an axis of rotation of the reel oriented substantially parallel to the first plane, the axis of rotation of the reel thereby substantially lying on a transverse plane with respect to the fixed bone segment; and
        a transmission driving the reel in order to wind up the cable.

2. The orthopedic bone transport system according to claim 1, wherein the transmission is a worm gear mechanism.

3. The orthopedic bone transport system according to claim 2, wherein the transmission comprises at least one irreversible kinematic pair.

4. The orthopedic bone transport system according to claim 2, wherein the worm gear mechanism comprises:
    a worm rotatably fixed to the main body; and
    a worm gear rotatably fixed to the main body and engaging with said worm,
    said reel rotating integrally with said worm gear.

5. The orthopedic bone transport system according to claim 4, wherein the cable pulling device further comprises a knob to transmit a rotating motion to said worm.

6. The orthopedic bone transport system according to claim 5, wherein said knob has a lock that locks the rotation of the knob with respect to the main body at given locking angular positions of the knob.

7. The orthopedic bone transport system according to claim 6, wherein the locking angular positions correspond to fixed angular increments in the rotation of the knob.

8. The orthopedic bone transport system according to claim 4, further comprising a motor coupled with the worm to drive the rotation of the worm and a controller for controlling the motor, wherein the controller is configured to control an activation frequency of the motor and a rotation angle of the worm driven by the motor for each activation of the motor.

9. The orthopedic bone transport system according to claim 1, wherein the reel comprises a spiral groove on its external surfaces to receive the cable as it winds up, preventing overlapping.

10. The orthopedic bone transport system according to claim 1, further comprising a force sensor directly or indirectly coupled to the cable for sensing a tension force acting on the cable.

11. The orthopedic bone transport system according to claim 1, wherein the main body is configured to be secured to the external fixation frame with the reel positioned between adjacent fixation rings of the external fixation frame.

12. The orthopedic bone transport system according to claim 1, wherein the reel is configured to retain tension in the cable as the transport bone segment is moved towards the fixed bone segment.

13. The orthopedic bone transport system according to claim 12, wherein the transmission permits the reel to rotate in a first direction and prevents the reel from rotating in an opposing second direction.

14. A cable pulling device for an orthopedic bone transport system, comprising:

a main body configured to be secured to an external fixation frame solidly attached to at least a fixed bone segment;

a reel rotatable about said main body and configured to wind up a cable to be secured to a transport bone segment to move said transport bone segment towards said fixed bone segment;

a transmission driving the reel in order to wind up the cable, wherein the transmission is a worm gear mechanism comprising:

a worm rotatably fixed to the main body; and a worm gear rotatably fixed to the main body and engaging with said worm, said reel rotating integrally with said worm gear; and a knob to transmit a rotating motion to said worm, wherein said knob has a lock that locks the rotation of the knob with respect to the main body at given locking angular positions of the knob, the locking angular positions corresponding to fixed angular increments in the rotation of the knob, wherein the lock comprises a regular polygon boss and a mating recess respectively provided on the knob and on the main body, or the other way around, wherein the rotation of the worm is prevented when the regular polygon boss is pressed into the mating recess, the lock further comprising an elastic element that biases the knob towards the main body.

15. A bone transport system, comprising:

an external fixation frame configured to be attached to at least a fixed bone segment with the external fixation frame oriented in a first plane;

at least one cable pulling device comprising:

a main body configured to be secured to the external fixation frame;

a reel rotatable about said main body and configured to wind up a cable to be secured to a transport bone segment to move said transport bone segment towards said fixed bone segment, wherein the main body is secured to the external fixation frame with an axis of rotation of the reel oriented substantially parallel to the first plane; and a transmission driving the reel in order to wind up the cable;

the cable pulling device being solidly attached to the external fixation frame; and an element for redirecting the cable, the element configured to be attached to the fixed bone segment and to redirect the cable departing from the at least one cable pulling device towards a transport bone segment.

16. The bone transport system according to claim 15, wherein said element for redirecting the cable is a fulcrum pin or screw.

17. The bone transport system according to claim 16, wherein the at least one cable pulling device comprises two cable pulling devices solidly attached to the external fixation frame in diametrically opposite positions, wherein the two cable pulling devices hold opposite ends of a same cable.

18. The bone transport system according to claim 17, wherein the cable enters the transport bone segment at its resected end and is attached thereto by means of an external loop, passing through at least one tangential hole made on the transport bone segment into its intermedullary canal following a longitudinal axis of the transport bone segment, enters the fixed bone segment from the intermedullary canal and, after orthogonal redirection around the fulcrum pin or screw, exits said fixed bone segment laterally.

19. The bone transport system according to claim 15, wherein the element for redirecting the cable is configured to extend within an intramedullary canal of the fixed bone segment.

20. A method for implanting a bone transport system that includes:

an external fixation frame;

two cable pulling devices each comprising:

a main body configured to be secured to the external fixation frame;

a reel rotatable about said main body and configured to wind up a cable; and a transmission driving the reel in order to wind up the cable; and an element for redirecting the cable;

the method comprising the steps of:

anchoring the external fixation frame at least to a first fixed bone segment;

mounting the two cable pulling devices at diametrically opposite positions on the external fixation frame, so that the two cable pulling devices face two opposite sides of the first fixed bone segment; and providing the cable which extends out from the reel of a first cable pulling device of the two cable pulling devices, enters the first fixed bone segment via a hole thereof, redirects in an axial direction of the first fixed bone segment at the element for redirecting the cable, enters a transport bone segment which is axially interposed between the first fixed bone segment and a second fixed bone segment, exits the transport bone segment via a hole thereof, loops around said transport bone segment, enters the transport bone segment via a hole thereof, extends back to the element for redirecting the cable, redirects toward a second cable pulling device of the two cable pulling devices, and is wound on the reel of the second cable pulling device.

* * * * *